(12) United States Patent
Huang et al.

(10) Patent No.: US 12,097,303 B2
(45) Date of Patent: Sep. 24, 2024

(54) DECELLULARIZED EXTRACELLULAR MATRIX, PREPARATION PROCESS AND USES THEREOF

(71) Applicant: National Tsing Hua University, Hsinchu (TW)

(72) Inventors: Chieh-Cheng Huang, Hsinchu (TW); Cheng-En Chiang, Hsinchu (TW); Yi-Qiao Fang, Hsinchu (TW); Chao-Ting Ho, Hsinchu (TW); Yu-Chieh Wang, Hsinchu (TW); Anna Blocki, Shatin (HK)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 281 days.

(21) Appl. No.: 17/198,895

(22) Filed: Mar. 11, 2021

(65) Prior Publication Data

US 2022/0211908 A1 Jul. 7, 2022

(30) Foreign Application Priority Data

Jan. 4, 2021 (TW) ................. 110100186

(51) Int. Cl.
| | |
|---|---|
| *A61L 27/36* | (2006.01) |
| *A61K 9/127* | (2006.01) |
| *A61K 38/18* | (2006.01) |
| *A61K 38/19* | (2006.01) |
| *A61L 27/38* | (2006.01) |
| *A61L 27/54* | (2006.01) |
| *A61B 17/12* | (2006.01) |

(52) U.S. Cl.
CPC .......... *A61L 27/3633* (2013.01); *A61K 9/127* (2013.01); *A61K 38/1866* (2013.01); *A61K 38/19* (2013.01); *A61L 27/36* (2013.01); *A61L 27/3683* (2013.01); *A61L 27/3687* (2013.01); *A61L 27/3834* (2013.01); *A61L 27/54* (2013.01); *A61B 17/12181* (2013.01); *A61L 2300/414* (2013.01); *A61L 2430/34* (2013.01); *A61L 2430/40* (2013.01)

(58) Field of Classification Search
CPC .. A61L 27/3633; A61L 27/36; A61L 27/3683; A61L 27/3687; A61L 27/3834; A61L 27/54; A61L 2300/414; A61L 2430/34; A61L 2430/40; A61K 9/127; A61K 38/1866; A61K 38/19; A61B 17/12181
USPC .......................................................... 424/572
See application file for complete search history.

(56) References Cited

U.S. PATENT DOCUMENTS

2006/0210597 A1* 9/2006 Hiles ............... A61L 31/047
                                                    623/2.14
2018/0361025 A1* 12/2018 Lancaster ............... A61L 27/34

FOREIGN PATENT DOCUMENTS

CA      3057498      * 10/2018

OTHER PUBLICATIONS

Chen et al., Applying macromolecular crowding to enhance extracellular matrix deposition and its remodeling in vitro for tissue engineering and cell-based therapies, Advanced Drug Delivery Reviews, vol. 63, (2011), pp. 277-290.*
Zhang et al., Coculture of mesenchymal stem cells and endothelial cells enhances host tissue integration and epidermis maturation through AKT activation in gelatin methacryloyl hydrogel-based skin model, Acta Biomaterialia, vol. 59, (2017), pp. 317-326.*
Wikipedia, Deoxyribonuclease, Accessed Feb. 20, 2024, Available online at: en.wikipedia.org/wiki/Deoxyribonuclease#:~:text=Deoxyribonuclease%20(DNase%2C%20for%20short),DNA%20backbone%2C%20thus%20degrading%20DNA.*

* cited by examiner

*Primary Examiner* — Jennifer M. H. Tichy
(74) *Attorney, Agent, or Firm* — WPAT, PC

(57) ABSTRACT

The present disclosure provides a decellularized extracellular matrix, the preparation process and uses thereof. The decellularized extracellular matrix of the present disclosure is derived from a three-dimensional cell spheroid, and the decellularized extracellular matrix has a three-dimensional spherical structure. The decellularized extracellular matrix of the present disclosure can be used to prepare a biomedical material scaffold for promoting tissue regeneration and repair.

1 Claim, 15 Drawing Sheets

(13 of 15 Drawing Sheet(s) Filed in Color)

DECELLULARIZED EXTRACELLULAR MATRIX, PREPARATION PROCESS AND USES THEREOF

CROSS-REFERENCE TO RELATED APPLICATION

This application claims priority of Taiwan patent application No. 110100186, filed on Jan. 4, 2021, the content of which is incorporated herein in its entirety by reference.

BACKGROUND OF THE INVENTION

1. Field of the Invention

The present invention relates to a decellularized extracellular matrix, the preparation process and uses thereof.

2. The Prior Art

The biomedical scaffold, which is often used in regenerative medicine and tissue repair in clinical research, can be divided into artificial polymers and natural polymers. Synthetic polymer materials are most widely used in polyglycolic acid, polylactic acid, polylactic acid-glycolic acid, and polycaprolactone. They have the advantages of biocompatibility, biodegradability, and precise control. The disadvantage is that it cannot construct a microstructure and components similar to the extracellular matrix (ECM), so the potential for promoting cell growth and tissue regeneration is limited.

Although natural polymers, such as collagen and hyaluronic acid extracted from animal tissues, are all components of ECM, the structure and composition of natural ECM are quite complex, and only a few kinds of ECM molecules cannot perfectly simulate the in vivo environment. Therefore, it is impossible to provide an appropriate niche to effectively support the various functions of cells or promote tissue regeneration. How to construct a natural tissue-like matrix scaffold is an unsolved problem in the art of regenerative medicine.

In order to overcome the inability of polymer materials to completely establish the matrix microenvironment inside tissues, the prior art has used biological tissues and even organs as raw materials and decellularized them as a bioactive scaffold. Although decellularized tissues have been used in clinical practice, there are still many shortcomings and safety risks that need to be faced, such as immune rejection, disease transmission, quality differences between batches, and size limitations. In addition, due to the characteristics of the source tissue, the decellularized tissue cannot be used for the repair of various target tissues.

In order to solve the problems faced by the above-mentioned decellularized scaffolds derived from biological tissues, the prior art used a matrix produced by two-dimensional in vitro culture of cells as a scaffold. However, the two-dimensional culture method takes a long time (weeks to months), and the decellularized extracellular matrix (dECM) produced is quite thin and fragile, which is not conducive to subsequent operations and use. In addition, the size of the dECM formed by two-dimensional culture is not only limited by the size of the culture container, but its microstructure is quite different from that of the three-dimensional dECM.

In order to solve the above-mentioned problems, those skilled in the art urgently need to develop novel and effective decellularized extracellular matrix for tissue regeneration and repair, the preparation process thereof and biomedical scaffolds for the benefit of a large group of people in need thereof.

SUMMARY OF THE INVENTION

A primary objective of the present invention is to provide a decellularized extracellular matrix derived from a three-dimensional cell spheroid, having a three-dimensional spherical structure.

Another objective of the present invention is to provide a method for preparing a decellularized extracellular matrix, comprising: (a) culturing a plurality of cells in vitro to construct a three-dimensional cell spheroid; and (b) subjecting a decellularization treatment to the three-dimensional cell spheroid by using an alkaline non-ionic surfactant and a deoxyribonuclease to obtain the decellularized extracellular matrix, wherein the decellularized extracellular matrix has a three-dimensional spherical structure.

According to an embodiment of the present invention, the decellularized extracellular matrix comprises at least one bioactive component.

According to an embodiment of the present invention, the at least one bioactive component is a growth factor, a cytokine or an exosome.

According to an embodiment of the present invention, the decellularized extracellular matrix further comprises a collagen I, a fibronectin, and a laminin.

According to an embodiment of the present invention, the growth factor is a vascular endothelial growth factor (VEGF).

According to an embodiment of the present invention, the decellularized extracellular matrix is subjected to a decellularization treatment by using an alkaline non-ionic surfactant and a deoxyribonuclease.

According to an embodiment of the present invention, a plurality of cells are attached to a surface of the decellularized extracellular matrix to perform proliferation.

According to an embodiment of the present invention, the three-dimensional cell spheroid is a three-dimensional cell spheroid formed by a plurality of cells.

According to an embodiment of the present invention, the method further comprises using at least one carbohydrate-based macromolecule to induce macromolecular crowding (MMC) for increasing deposition of extracellular matrix and the at least one bioactive component by the plurality of cells during constructing the three-dimensional spheroid.

Another objective of the present invention is to provide a method for promoting tissue regeneration and repair, comprising administering to a subject in need thereof a composition comprising an effective amount of the aforementioned decellularized extracellular matrix.

According to an embodiment of the present invention, the decellularized extracellular matrix is used for preparing a biomedical scaffold.

In summary, the effect of the decellularized extracellular matrix of the present invention is that since the matrix is made of three-dimensionally cultured cells, its components and microstructure are quite similar to those in biological tissues. The experimental results show that cells can be effectively attached to the surface of the three-dimensional decellularized extracellular matrix and perform proliferation. Since the three-dimensional decellularized extracellular matrix contains bioactive components secreted by many cells, such as growth factors, cytokines, and exosomes, it has the function of regulating the behavior of subsequent attached cells. By changing the types of cells that construct three-dimensional cell spheroids or controlling cell behavior, the composition of the bioactive molecules remaining in the three-dimensional decellularized extracellular matrix is not the same, so it has a wide range of applications, such as the use of stem cells. When a three-dimensional spheroid is established, the remaining bioactive molecules can contribute to the occurrence of angiogenesis and tissue regeneration. With the macromolecular crowding (MMC) induced by carbohydrate-based macromolecules, the total amount of extracellular matrix (ECM) and growth factor secretion in the three-dimensional cell spheroids can be significantly increased, which in turn makes the content of ECM molecules and growth factors in the subsequent derived decellularized extracellular matrix increased, further enhancing the biological activity of the decellularized extracellular matrix. In addition, each three-dimensional decellularized extracellular matrix can be regarded as a small scaffold with the same size as the three-dimensional cell spheroid before decellularization, so three-dimensional decellularized extracellular matrix with different diameters can be prepared according to requirements. After the cells are cultured in a three-dimensional decellularized extracellular matrix, they can be used as a carrier for cell transmission (for example, transplanting a three-dimensional decellularized extracellular matrix containing cells to the site to be treated by injection), a plurality of three-dimensional decellularized extracellular matrices can be assembled into a large structure in a variety of ways. Since the three-dimensional decellularized extracellular matrix is relatively easy to manufacture in large quantities, the large-scale stents formed by polymerization are not limited in shape and size, and can be highly customized. Furthermore, because the cells are first cultured on individual three-dimensional decellularized extracellular matrix, the aggregated cells can be evenly distributed in the entire large scaffold structure, solving the uneven distribution of cells encountered in traditional tissue engineering.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1A:
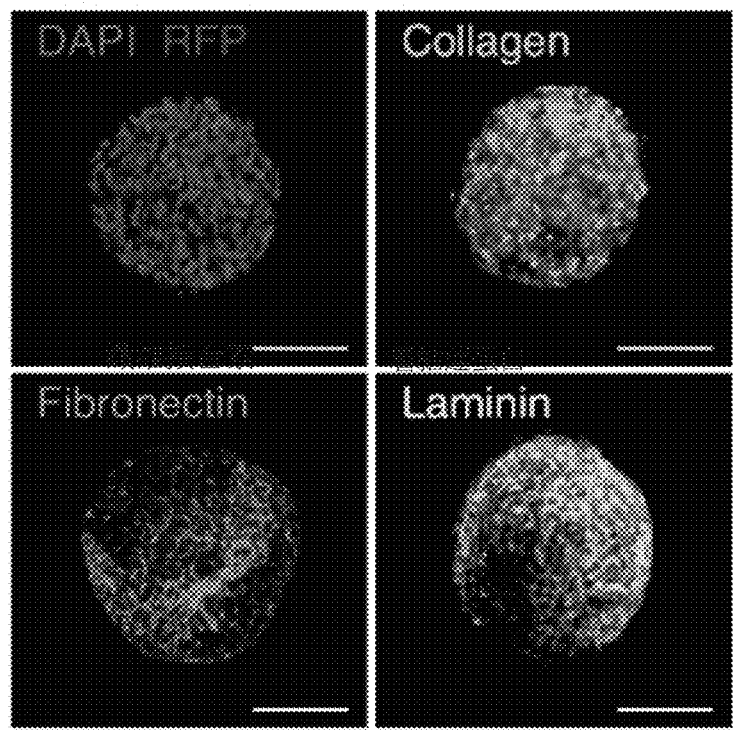
FIG. 1A shows confocal fluorescence images of the three-dimensional cell spheroid, in which DAPI represents 4',6-diamidino-2-phenylindole, a fluorescent dye which can bind strongly to DNA; RFP represents red fluorescence protein; scale bars, 100 μm.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

Data are expressed as the mean±standard deviation (SD). All p-values were calculated using One-way ANOVA followed by Tukey's correction. Statistical analyses were conducted using GraphPad Prism software (version 8.4.3; San Diego, CA, USA). Differences were considered to be significant at p<0.05.

Human umbilical cord blood MSCs and human umbilical cord vein endothelial cells (HUVECs) used in the following examples were acquired from the Bioresource Collection and Research Center (BCRC), Food Industry Research and Development Institute, Hsinchu, Taiwan. MSCs expressed red fluorescent protein (RFP) under the control of CMV promoter (pDsRed-N1 vector), allowing easy cell tracking (see C. J. Hung, C. L. Yao, F. C. Cheng, et al., Establishment of immortalized mesenchymal stromal cells with red fluorescence protein expression for in vivo transplantation and tracing in the rat model with traumatic brain injury, Cytotherapy 12(4) (2010) 455-465). The MSCs were maintained in minimum essential medium a (Thermo Fisher Scientific, Waltham, MA, USA) that was supplemented with 20% fetal bovine serum (FBS; GE Healthcare Bio-Sciences, Pittsburgh, PA, USA), 4 ng/mL basic fibroblast growth factor (PeproTech, Rocky Hill, NJ, USA), 30 mg/mL hygromycin B and 200 mg/mL geneticin (both from Thermo Fisher Scientific). HUVECs were cultivated in endothelial cell growth medium (EGM)-2 (Lonza Walkersville, MA, USA). Cells were incubated in a humidified incubator at 37° C. with 5% $CO_2$.

Example 1

Preparation, Configuration and Analysis of Bioactive Components of Decellularized Extracellular Matrix (dECM)

The operation process of immunofluorescence staining used in this example is as follows. 3D cell spheroids or the derived dECM scaffolds were fixed for 20 min with 4% paraformaldehyde (Sigma-Aldrich). After permeabilization with 0.5% Triton X-100 and blocking with 5% normal goat serum (Vector Laboratories, Burlingame, CA, USA) at room temperature for 2 h, the samples were incubated with primary antibodies against vascular endothelial growth factor (VEGF), fibronectin, laminin, and collagen (all from Genetex, Hsinchu, Taiwan) in 5% bovine serum albumin (BSA; Sigma-Aldrich) at 4° C. overnight. After three washes in PBS (5 min each), Alexa Fluor 488- or Alexa Fluor 633-conjugated secondary antibodies (Thermo Fisher Scientific) were applied at 4° C. overnight. Finally, the test samples were washed with PBS, counterstained with 4',6-diamidino-2-phenylindole (DAPI; Thermo Fisher Scientific), mounted with a tissue-clearing solution (FocusClear solution, CelExplorer, Hsinchu, Taiwan), and observed with a confocal microscope (LSM 780; Carl Zeiss, Oberkochen, Germany).

The operation process of DNA quantification used in this example is as follows. To determine DNA content, 25 cell spheroids or dECM scaffolds were lysed using 200 µL of digestion buffer (10 mM Tris-HCl and 1 mM EDTA) with 0.1 mg/mL proteinase K (Sigma-Aldrich) at 50° C. overnight. The amount of DNA in lysates was quantified using the Quant-iT PicoGreen dsDNA Quantitation kit (Thermo Fisher Scientific) according to the manufacturer's instructions. Briefly, Quant-iT PicoGreen reagent was added to the lysates and incubated for 5 mM followed by fluorescence measurement using a microplate reader (SpectraMax iD3, Molecular Devices, Sunnyvale, CA, USA) at an excitation wavelength of 480 nm and an emission wavelength of 520 nm. The absolute DNA content was determined against a standard curve generated using lambda DNA (Thermo Fisher Scientific).

The operation process of enzyme-linked immunosorbent assay (ELISA) used in this example is as follows. An ELISA kit (RayBiotech, Peachtree Corners, GA, USA; Cat. No. ELH-VEGF-CL) designed to determine the concentration of VEGF in lysates was employed in this example. Briefly, 25 cell spheroids or dECM scaffolds were lysed using 200 µL of lysis buffer (provided by the manufacturer). After centrifugation at 4,500 rpm for 10 min, the total protein level of the supernatant was quantified using the bicinchoninic acid assay (G-Biosciences, St. Louis, MO, USA). Subsequently, all test samples were standardized to 20 µg of total protein in 100 µL of buffer, and their VEGF content was quantified according to the manufacturer's manual.

The 3D mesenchymal stem cell (MSC) spheroids were fabricated using a methylcellulose (MC) hydrogel-based method. Briefly, 50 µL of 12% (w/v) MC (Sigma-Aldrich, St. Louis, MO, USA) solution prepared in 0.5× phosphate buffered saline (PBS; Sigma-Aldrich) was loaded into each well in 96-well plates and heated to 37° C. for 30 min MSC suspensions were prepared by mild trypsinization of confluent cells using TrypLE reagent (Thermo Fisher Scientific). The cells were then diluted to the desired cell densities using culture medium. Alternatively, culture medium that was supplemented with Ficoll 70 (37.5 mg/mL; Cytiva, Marlborough, MA), Ficoll 400 (25 mg/mL; Cytiva), Ficoll mixture (37.5 mg/mL Ficoll 70 and 25 mg/mL Ficoll 400), or dextran sulfate (DxS, MW: 500 kDa; 10 µg/mL; Sigma-Aldrich; D8906) was used to suspend MSCs to induce an excluded volume effect by macromolecular crowding (MMC). Finally, 150 µL of the MSC suspension was transferred into each well of the MC-loaded 96-well plates and incubated for 24 h for spheroid assembly.

After 24 h incubation, a 3D cell spheroid was observed in each well. The confocal images indicated that the MSCs deposited various ECM proteins, including collagen I, fibronectin and laminin, within the formed 3D cell spheroids (see FIG. 1A), indicating their potential to serve as a source for cell-derived dECM scaffolds.

Figure 1B:
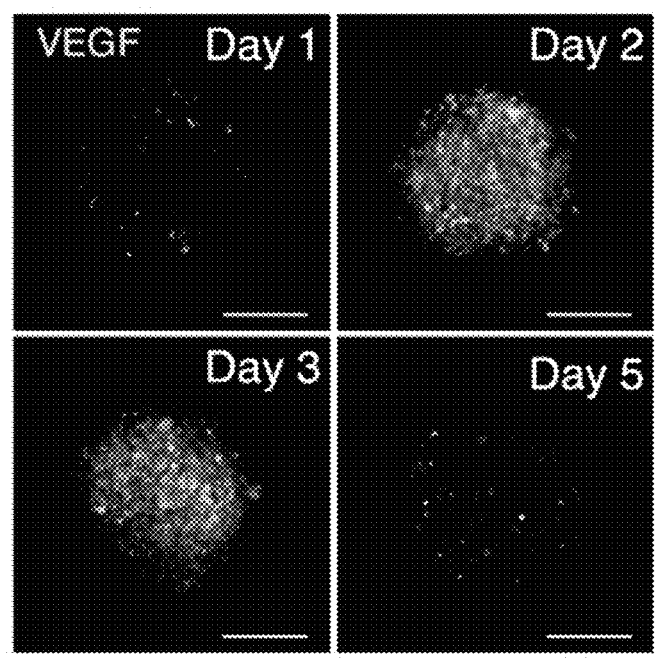
FIG. 1B shows representative confocal images of vascular endothelial growth factor (VEGF) within 3D cell spheroids; scale bars, 100 μm.
Figure 1C:
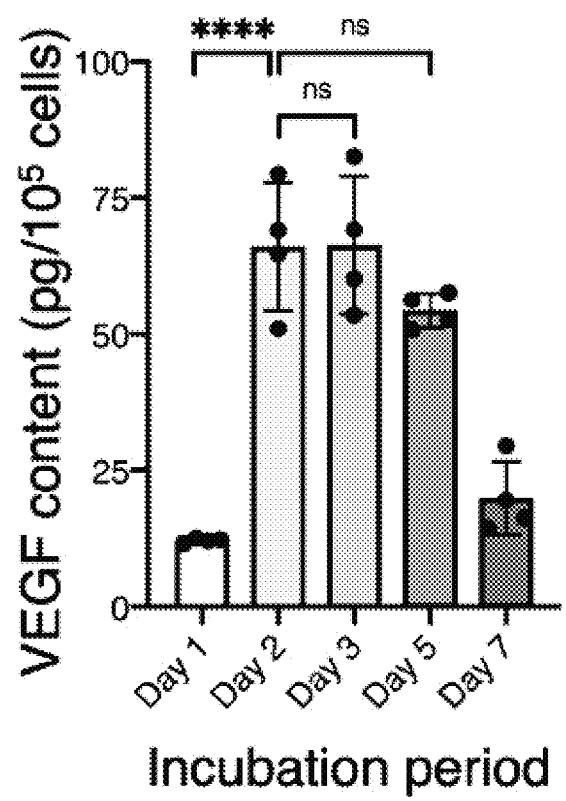
FIG. 1C shows corresponding quantitative results determined using enzyme-linked immunosorbent assay (ELISA; n=4), in which **** represents $p<0.001$; ns, not significant.

Before processing the spheroids for decellularization, the invention attempted to maximize the content of bioactive molecules secreted by MSCs within the cell spheroids by prolonging the incubation period. Herein, VEGF was chosen as the target factor since the VEGF-induced angiogenesis creates a nascent vasculature that is crucial for subsequent graft integration and tissue regeneration. VEGF within spheroids was detected by immunofluorescence microscopy (see FIG. 1B) and quantified by ELISA (FIG. 1C). As can be seen from FIGS. 1B and 1C, after cell spheroid assembly, the VEGF content increased and reached a plateau within 2 days (a 5.4-fold elevation compared to Day 1, $p<0.001$), while prolonged incubation led to a significant decrease in VEGF levels. Therefore, 3D MSC spheroids that were formed at 48 h post-seeding were employed for subsequent experiments.

The decellularized extracellular matrix (dECM) derived from 3D cell spheroids was subsequently prepared. The cell spheroids were collected and processed to remove the cellular and nuclear contents. The cells within the harvested 3D spheroids were stripped by using an alkaline detergent treatment or a freeze-thaw cycling method. Herein, two different approaches, the freeze-thaw cycling method and Triton X-100 treatment, were employed. Both methods displayed high efficiency in removing the nuclear and cellular content, as indicated by the dramatically decreased fluorescence intensity of DAPI and RFP respectively (see FIG. 2A). For multiple freeze-thaw cycles, the harvested cell spheroids were suspended in PBS in centrifuge tubes, which were cooled to −80° C. for 30 min and thawed in a 37° C. water bath. This procedure was repeated three times. For the detergent-based method, cell spheroids were immersed in decellularization solution that contained 0.5% (v/v) Triton X-100 (Sigma-Aldrich) and 20 mM ammonium hydroxide and incubated at room temperature for 1 h. After three PBS washes, both procedures were followed by incubation with 1 kU/mL DNase I (Sigma-Aldrich) for 30 mM at 37° C. and rinse twice with PBS before further applications.

Figure 2A:
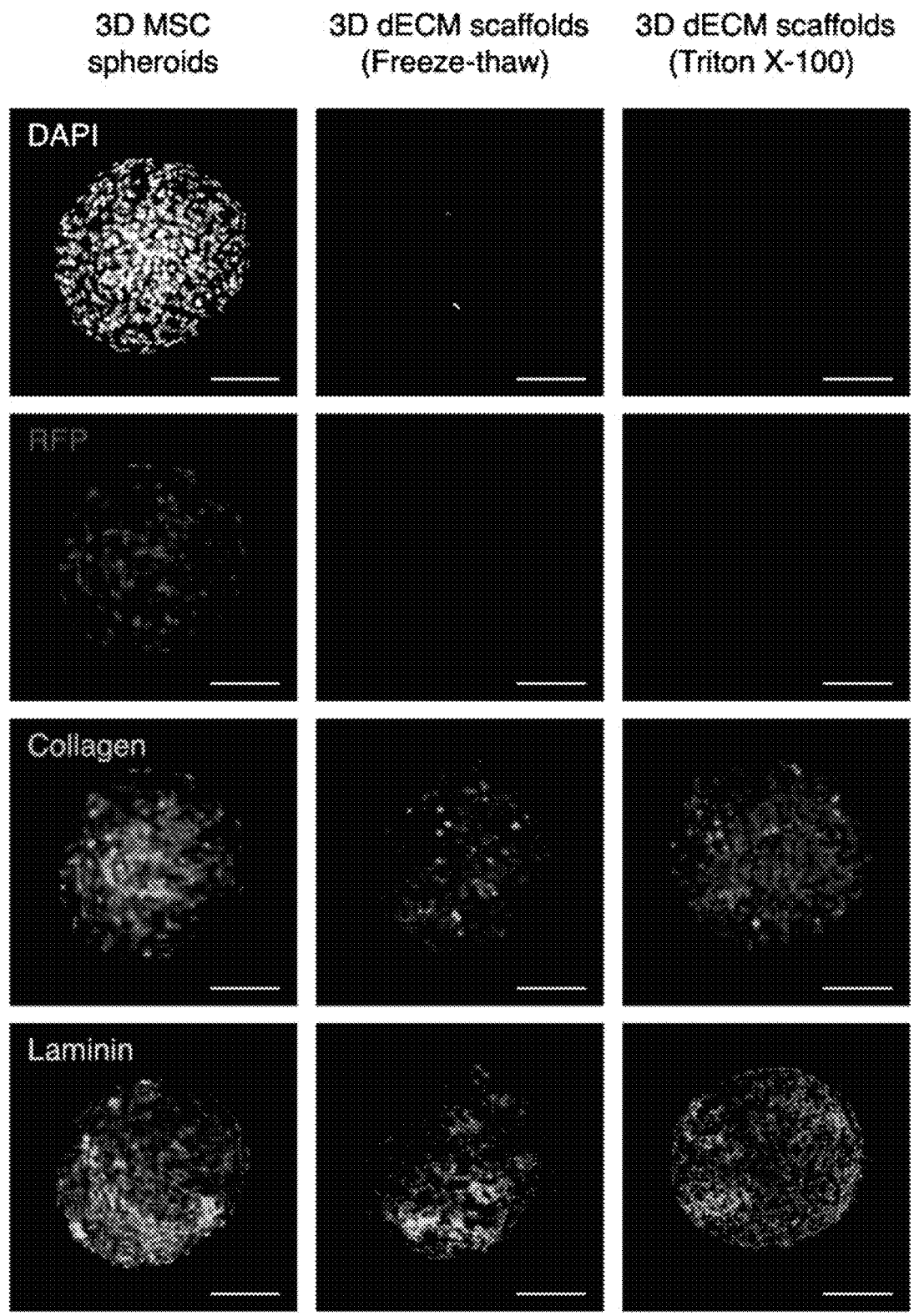
FIG. 2A shows representative fluorescence images of 3D MSC spheroids before and after decellularization. Scale bars, 100 μm.
Figure 2B:
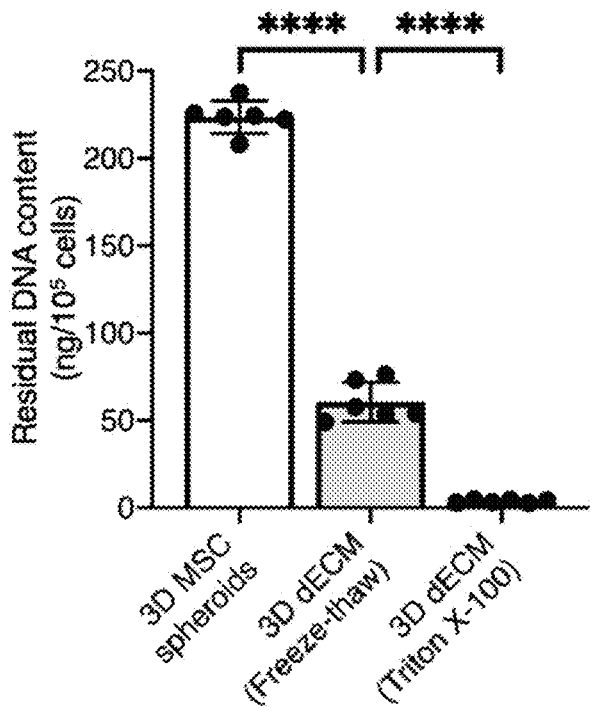
FIG. 2B shows remnant content of DNA within the 3D decellularized extracellular matrix (dECM) scaffolds determined by the PicoGreen assay (n=6) and ELISA (n=4), in which **** represents $p<0.001$.
Figure 2C:
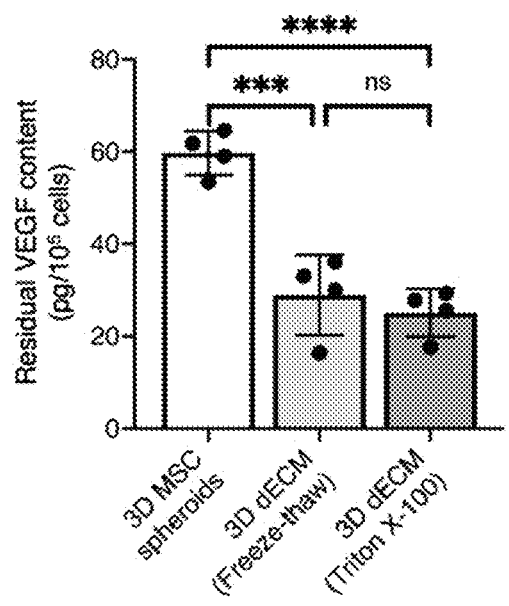
FIG. 2C shows remnant content of VEGF within the 3D decellularized extracellular matrix (dECM) scaffolds determined by the PicoGreen assay (n=6) and ELISA (n=4), in which ** represents $p<0.001$; * represents $p<0.005$; ns, not significant.

Moreover, the deposited ECM proteins and their gross framework were preserved, as revealed by the fluorescence images of collagen I and laminin (see FIG. 2A). This example then further quantified the amount of remnant DNA (see FIG. 2B) or VEGF (see FIG. 2C). The results show that the levels of residual VEGF in the groups were comparable (see FIG. 2C). However, freeze-thaw cycling with DNase I treatment removed only 72.9% of the host DNA, while the Triton X-100-based extraction method eliminated 98.1% of the total dsDNA (see FIG. 2B). Because a host DNA removal rate of at least 90% should be achieved to prevent immunorejection of the dECM scaffold, alkaline Triton X-100 was used in the following experiments.

Example 2

Size Optimization of Decellularized Extracellular Matrix (dECM)

As a large spheroid size makes it difficult to ensure high efficiency in removing nuclear materials, which is important for scaffold preparation, this example further optimized the diameters of the spheroids by modulating the cell seeding densities. 3D MSC spheroids prepared with various cell seeding densities (5,000, 7,000, 10,000 and 12,000 cells per spheroid) were processed for decellularization followed by DNA quantification. As indicated by the fluorescence images (see FIG. 3A) and the results of the PicoGreen assay (see FIG. 3B), the diameters of the grown cell spheroids and their DNA content increased with increasing cell seeding density. After decellularization, cell spheroids fabricated with 5,000 and 7,000 cells displayed a higher DNA removal rate (97.8% and 94.7%, respectively) than did those prepared with 10,000 and 12,000 cells (85.7% and 84.6%, respectively; FIG. 3B). Therefore, 3D MSC spheroids fabricated with 7,000 cells per spheroid were employed for the subsequent experiments.

Example 3

Evaluation of Effect of Supplementation with Macromolecules on Enhancing Extracellular Matrix (ECM) Deposition by MSCs in 3D The operation process of Western blotting analysis used in this example is as follows. Test samples (25 cell spheroids or dECM scaffolds) were lysed by incubating with 200 μL of RIPA buffer (20 mM Tris-HCl, 1 mM EGTA, 150 mM NaCl, and 1% Triton X-100) containing protease inhibitor cocktail tablets (Sigma-Aldrich). The lysates were denatured at 95° C. for 10 mM, resolved via sodium dodecyl sulfate (SDS)-polyacrylamide gel electrophoresis in an 8% acrylamide gel (Bio-Rad Laboratories, Hercules, CA, USA) with an 80 V resolving voltage, and transferred to a polyvinylidene difluoride membrane. After blocking with 5% skim milk for 1 h and incubating with primary antibodies against fibronectin or laminin overnight, the membrane was detected using the Amersham ECL Select Western Blotting Detection Reagent (Cytiva) using HRP-conjugated secondary antibodies (GeneTex).

Figure 4A:
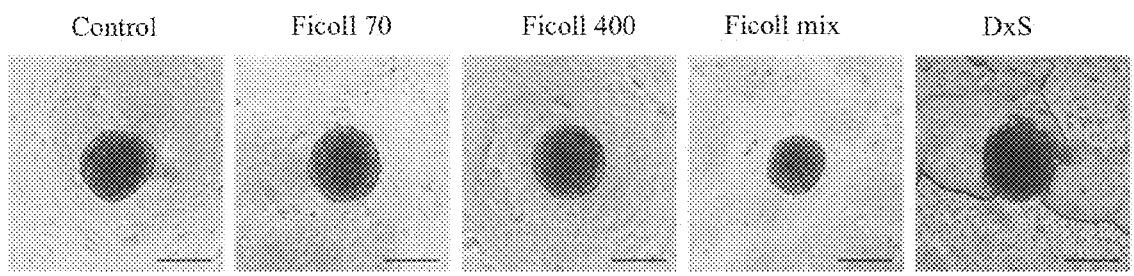
FIG. 4A shows phase-contrast microphotographs of 3D MSC spheroids supplemented with various crowding agents (Ficoll 70, Ficoll 400, Ficoll mixture (mix), or dextran sulfate (DxS)) during assembly. Scale bars, 200 μm.

Carbohydrate-based macromolecules, Ficolls and DxS, were shown to amplify ECM deposition in 2D culture via MMC or co-precipitation. In order to investigate if these macromolecules would have a comparable effect on ECM accumulation in 3D, MSCs were exposed to Ficolls or DxS while assembling into 3D spheroid configurations on the surface of MC hydrogels. This example utilized concentrations of the macromolecules as established previously for 2D cultures. The DxS was supplemented at 100 μg/mL, and the Ficolls were added as a mixture of Ficoll 400 at 25 mg/mL and Ficoll 70 at 37.5 mg/mL. In addition to that, this example also explored the effect of each of the Ficoll species by itself at the established concentrations. Morphologically, the 3D MSC spheroids with MMC were similar to those obtained with the control condition (see FIG. 4A) and had a diameter around 270 μm (Table 1), except that in the Ficoll mixture group, which had a significantly smaller size. Table 1 shows the mean sizes of the 3D MSC spheroids fabricated with or without crowding agents (n=30 spheroids pooled from 5 batches). * $p<0.05$ vs. control group.

TABLE 1

| Group | Control | Ficoll 70 | Ficoll 400 | Ficoll mixture | DxS |
|---|---|---|---|---|---|
| Diameter (μm) | 264.4 ± 17.1 | 264.9 ± 11.8 | 277.3 ± 9.9 | 204.4 ± 5.6* | 270.2 ± 8.2 |

Figure 4B:
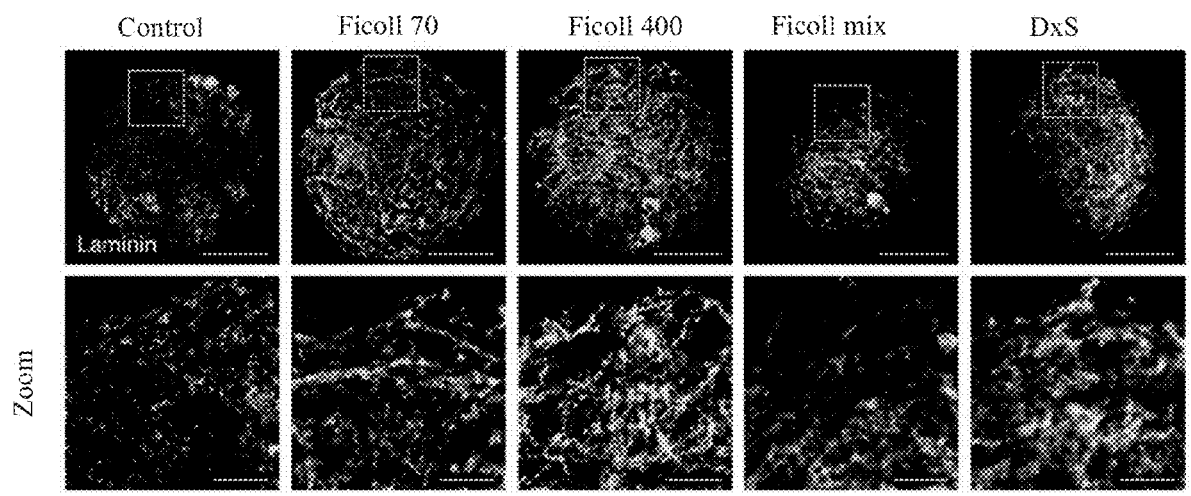
FIG. 4B shows fluorescence images of laminin staining of the 3D dECM scaffolds. Bottom panel, zoom into the region outlined by the white box. Scale bars, 100 μm; 20 μm (zoom panel).
Figure 4C:
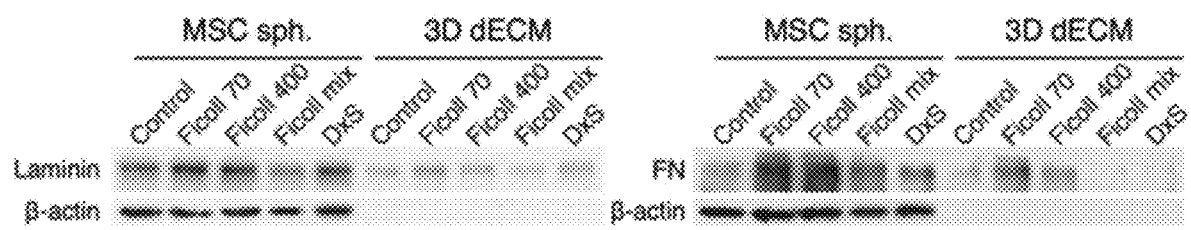
FIG. 4C shows the levels and corresponding residual ratios of laminin, fibronectin (FN; both were determined by Western blot); DxS represents dextran sulfate.
Figure 4D:
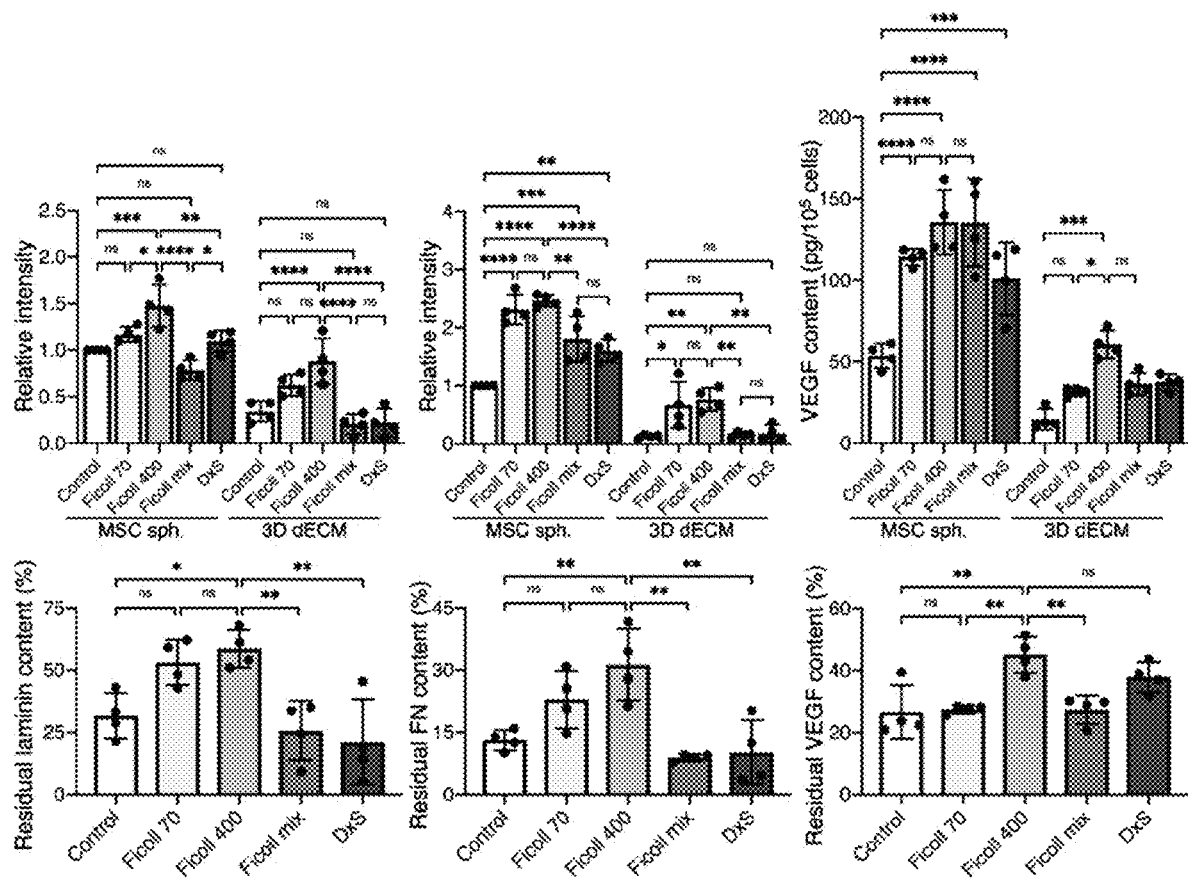
FIG. 4D shows VEGF (determined by ELISA) of 3D MSC spheroids and the derived dECM scaffolds treated with crowding agents (n=4). The amounts of fibronectin and laminin (relative to β-actin) were normalized to those of the untreated control. The percentage of residual content was defined as the ratio of the amount of target protein in 3D dECM scaffolds and that in 3D MSC spheroids; * represents $p<0.05$;  represents $p<0.01$; * represents $p<0.005$; **** represents $p<0.001$; ns, not significant.

These spheroids were collected, decellularized and analyzed for their laminin distribution and ECM protein content by immunostaining and western blotting, respectively. The results of laminin staining revealed that supplementation of macromolecules promoted the formation of an in vivo-like fibrillar or reticular ultrastructural organization with well-defined laminin fibers (see FIG. 4B). In contrast, control spheroids exhibited a diffuse staining of laminin with thin fibrils surrounding the cells (see FIG. 4B). Additionally, supplementation with Ficoll 70 and Ficoll 400 resulted in significantly increased laminin levels (5.3- and 6.1-fold increase compared to the control; $p<0.05$) of the 3D dECM scaffolds, and treatment with Ficoll 400 led to the maximum amount of fibronectin (2.6-fold enhancement relative to the control; $p<0.001$; FIG. 4C). By analyzing the amount of remaining VEGF within the dECM scaffolds using ELISA, this example found that all the MMC-treated groups exhibited elevated levels of VEGF, especially the Ficoll 400 group (4.2-fold increase compared to the control; $p<0.005$; FIG. 4D). Moreover, by comparing the amount of residual ECM proteins or VEGF in 3D dECM scaffolds with the corresponding 3D MSC spheroids, the Ficoll 400-treated groups exhibited a significantly enhanced potential in retaining these bioactive molecules ($p<0.05$; FIGS. 4C and 4D). Based on these analytic results, Ficoll 400 was employed as the crowding agent to induce MMC during 3D spheroid preparation.

Regarding MMC, it is generally believed that the best effect is dextran sulfate (DxS) or Ficoll mixture (or Ficoll cocktail; composed of Ficoll 70 and Ficoll 400) (see Chen C, Loe F, Blocki A, Peng Y, Raghunath M. Applying macromolecular crowding to enhance extracellular matrix deposition and its remodeling in vitro for tissue engineering and cell-based therapies. Adv Drug Deliv Rev 2011; 63:277-90; Gaspar D, Fuller K P, Zeugolis D I. Polydispersity and negative charge are key modulators of extracellular matrix deposition under macromolecular crowding conditions. Acta Biomaterialia 2019; 88:197-210; Kumar P, Satyam A, Fan X, Collin E, Rochev Y, Rodriguez B J, Gorelov A, Dillon S, Joshi L, Raghunath M, Pandit A, Zeugolis D I. Macromolecularly crowded in vitro microenvironments accelerate the production of extracellular matrix-rich supramolecular assemblies. Sci. Rep. 2015; 5). However, according to the experimental results of FIGS. 4C and 4D, the efficiency of DxS and Ficoll mixture in enhancing the deposition of extracellular matrix (ECM) in a three-dimensional environment is not as good as using Ficoll 400 alone.

Figure 3A:
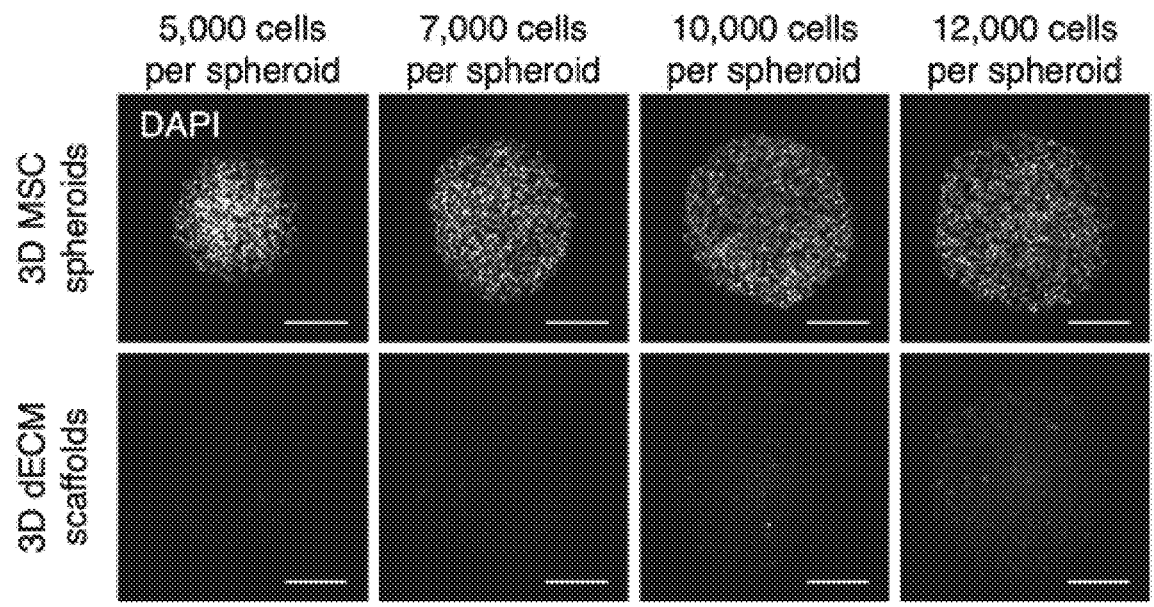
FIG. 3A shows representative DAPI staining images of 3D MSC spheroids fabricated using various numbers of cells before and after decellularization. Scale bars, 100 μm.
Figure 3B:
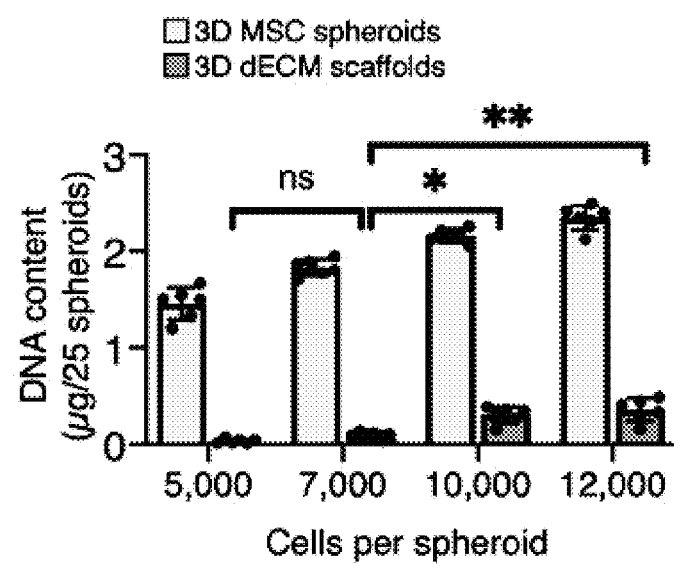
FIG. 3B shows corresponding DNA content of 3D MSC spheroids (n=6) fabricated using various numbers of cells before and after decellularization, in which * represents $p<0.05$; ** represents $p<0.01$; ns, not significant.

In the prior art, DxS at a concentration of 10 µg/mL, after 6 days of incubation, can increase the amount of fibronectin deposition twice that of the control group (see FIG. 3A in Assuncao M, Wong C W, Richardson J J, Tsang R, Beyer S, Raghunath M, Blocki A. Macromolecular dextran sulfate facilitates extracellular matrix deposition by electrostatic interaction independent from a macromolecular crowding effect. Mater Sci Eng C Mater Biol Appl 2020; 106:110280). In the results of FIGS. 4C and 4D of this example, adding the same concentration of DxS under the condition of three-dimensional culture can increase the deposition amount of fibronectin up to 1.85 times in only 2 days.

In addition, in the prior art, MMC would reduce the mobility of MSC (see Zeiger A S, Loe F C, Li R, Raghunath M, Van Vliet K J. Macromolecular Crowding Directs Extracellular Matrix Organization and Mesenchymal Stem Cell Behavior. PLoS ONE 2012; 7, FIG. 3D). However, according to the experimental results of FIG. 4E of this example, after MSCs aggregate into three-dimensional cell spheroids, their mobility is not affected by whether MMC is induced.

Figure 4E:
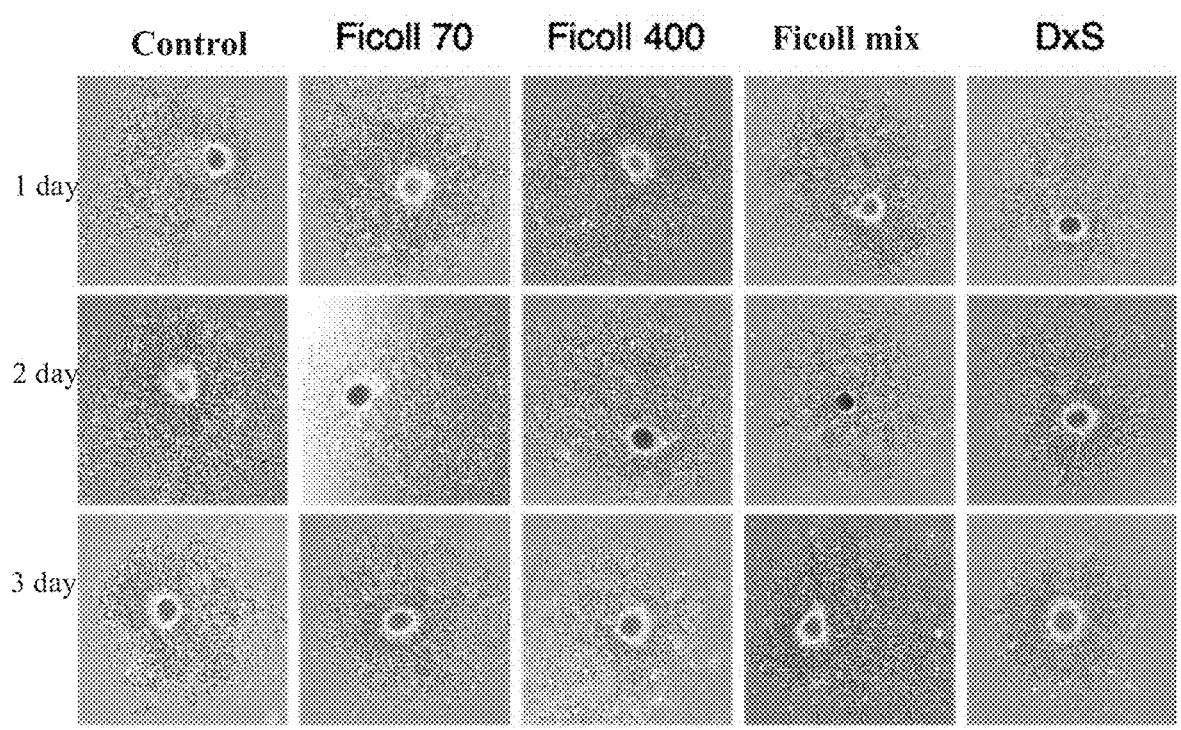
FIG. 4E shows phase-contrast microphotographs of 3D MSC spheroids supplemented with various crowding agents (Ficoll 70, Ficoll 400, Ficoll mixture (mix), or dextran sulfate (DxS)) during assembly.

FIG. 4E shows the observation of adding three-dimensional cell spheroids to the culture dish. There is no significant difference between the cell spheroid attachment and cell movement among the groups.

Example 4

Evaluation of Bioactivity Exhibited by 3D MSC Spheroid-Derived Decellularized Extracellular Matrix (dECM)

The operation process of cell proliferation assay and Matrigel tube formation assay used in this example is as follows. HUVECs suspended in Dulbecco's modified minimum essential medium (DMEM) supplemented with 10% FBS were plated into each well of a 6-well plate at a density of $2\times10^5$ cells/well and incubated for 4 h for cell adhesion. Subsequently, 50 3D dECM scaffolds were transferred into the wells for 24 h cultivation. Untreated HUVECs served as controls. The cells were photographed under a phase-contrast microscope (Carl Zeiss). Moreover, the proliferation of HUVECs was quantified using a cell counting kit-8 (Dojindo Molecular Technology, Kumamoto, Japan) according to the manufacturer's protocol.

Additionally, a Matrigel tube formation assay was performed by adding 10,000 HUVECs in DMEM with 10% FBS into a well that was precoated with 40 µL of growth factor-reduced (GFR) Matrigel (Corning, Corning, NY, USA) in a 96-well plate. After 4 h incubation, the cells in each well received 10 3D dECM scaffolds. The formed tubular structures were photographed and monitored for 3 days. The total length of the tubes was quantified using ImageJ software.

Figure 5A:
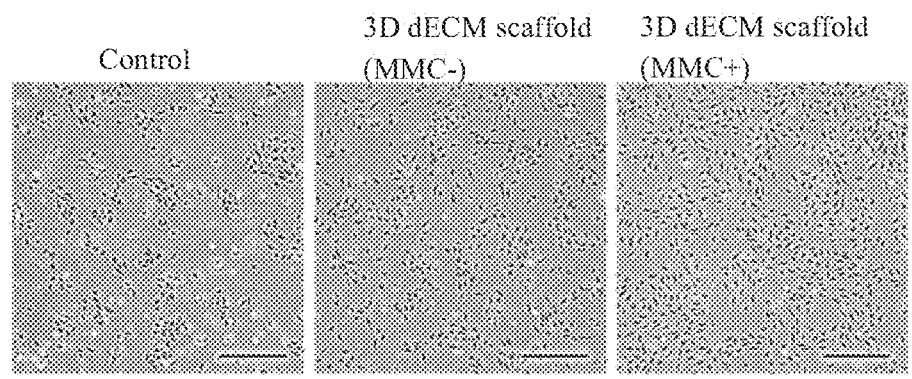
FIG. 5A shows representative phase-contrast images of human umbilical vein endothelial cells (HUVECs) treated with the prepared 3D dECM scaffolds. Scale bars, 400 μm. MMC+, scaffolds prepared with MMC. MMC−, scaffolds prepared without MMC.
Figure 5B:
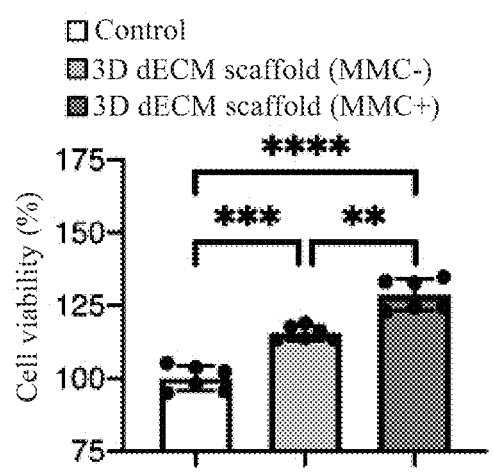
FIG. 5B shows corresponding quantitative analysis of cell proliferation (n=6).  represents $p<0.01$; * represents $p<0.005$; **** represents $p<0.001$; MMC+, scaffolds prepared with MMC; MMC−, scaffolds prepared without MMC.
Figure 5C:
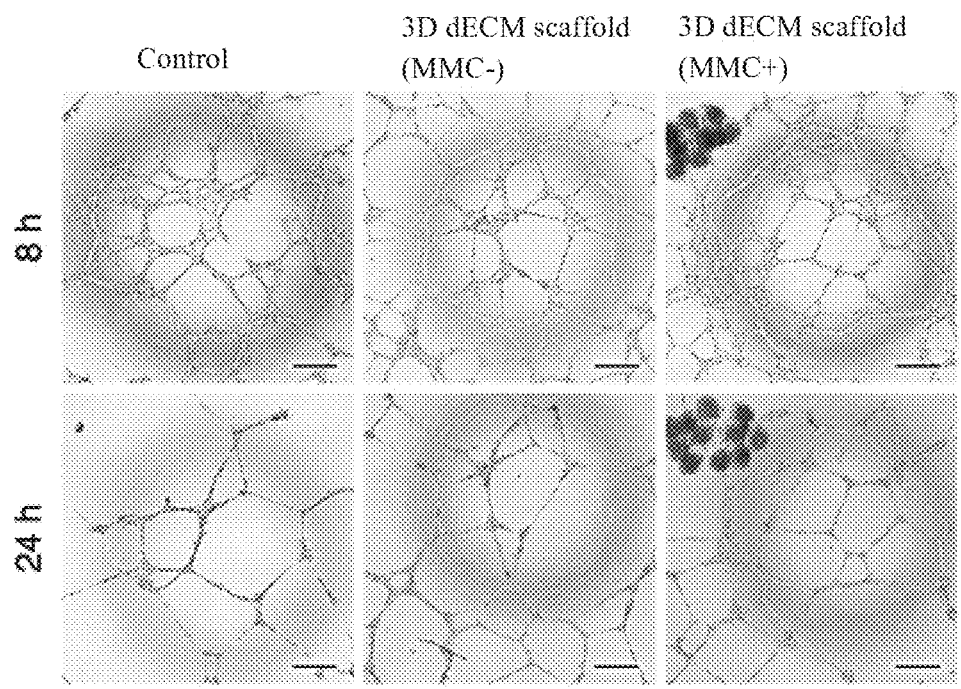
FIG. 5C shows tubular structures formed by HUVECs that received 3D dECM scaffolds on Matrigel. Scale bars, 400 μm. MMC+, scaffolds prepared with MMC. MMC−, scaffolds prepared without MMC.
Figure 5D:
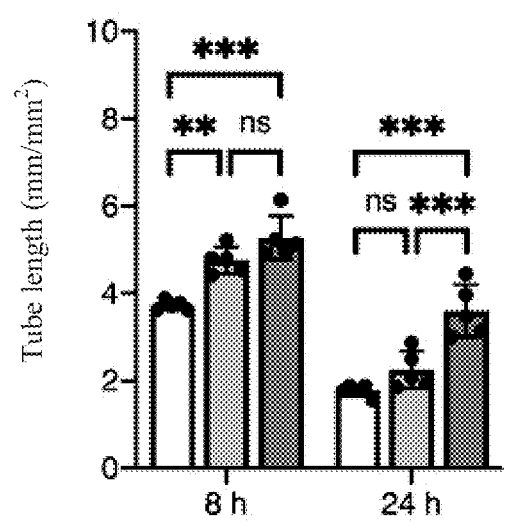
FIG. 5D shows corresponding total tube length (n=5).  represents $p<0.01$; * represents $p<0.005$; ns, not significant.

Since VEGF secreted by MSCs was retained throughout the decellularization procedure, this example next investigated whether these VEGF-loaded dECM scaffolds could influence endothelial cell behaviors. First, HUVECs were exposed to the dECM scaffolds, and untreated HUVECs were used as a control. The results showed that HUVECs displayed increased cell proliferation in response to the 3D dECM scaffolds (see FIGS. 5A and 5B). Moreover, the scaffolds prepared with MMC exhibited a significantly higher pro-proliferative potential (1.29-fold relative to untreated control) than those fabricated without MMC (1.16-fold compared to untreated control; $p<0.01$; FIG. 5B). Next, a Matrigel tube formation assay was further performed to verify the pro-angiogenic potential of the retained VEGF. By treating with the dECM scaffolds, the nascent tubular structures formed by HUVECs could be stabilized and thus persisted for a longer period, whereas swift regression of the grown tubular networks was observed in the untreated control group (see FIG. 5C). Analysis of the tube length corroborated the acquired imaging data (see FIG. 5D). Additionally, a 1.6-fold increase in tube length was observed in the group that received the dECM scaffolds with MMC, suggesting that these scaffolds had a pro-angiogenic potential superior to that of the scaffolds without MMC ($p<0.005$, FIG. 5D). Overall, these results demonstrated that soluble molecules such as VEGF that remained within the dECM scaffolds were bioactive and could be employed to modulate cellular functions and behaviors.

Example 5

3D MSC Spheroid-Derived dECM Serves as a Scaffold for Cellularization

The operation process of recellularization used in this example is as follows. To repopulate the scaffolds with cells, $1\times10^6$ HUVECs suspended in 100 µL of culture medium were added to a tube that contained 100 3D dECM scaffolds. After incubation at 37° C. for 1 h, the scaffolds were rinsed with PBS to remove unattached cells before being cultured in plates with an ultralow-attachment surface (Corning). After cultivation, the cell-laden scaffolds were processed for immunostaining using a primary antibody against CD31 (Agilent Technologies, Santa Clara, CA, USA).

Figure 6A:
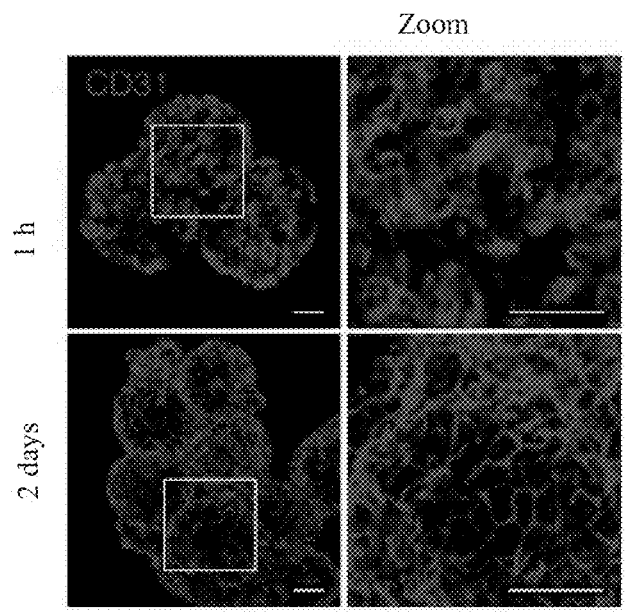
FIG. 6A shows maximum-intensity projected confocal images showing CD31-positive HUVECs grown on 3D dECM scaffolds for 1 h or 2 days. Scale bars, 50 μm.
Figure 6B:
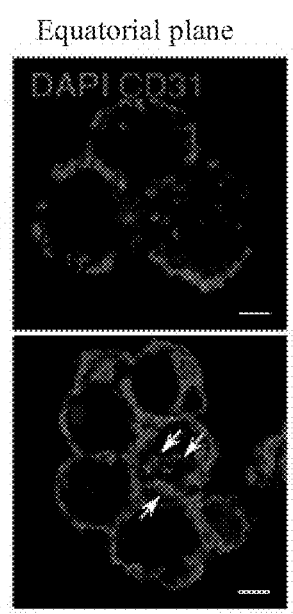
FIG. 6B shows representative optical sections of spheroid equatorial plane. White arrows indicate the cells grown into the interior of a 3D scaffold. Scale bars, 50 μm.
Figure 6C:
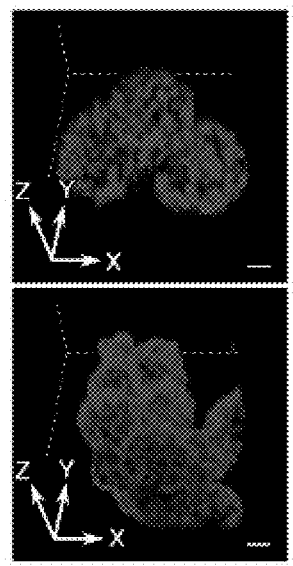
FIG. 6C shows 3D rendering from the assembled 3D dECM spheroids in FIG. 6A. Scale bars, 50 μm.
Figure 6D:
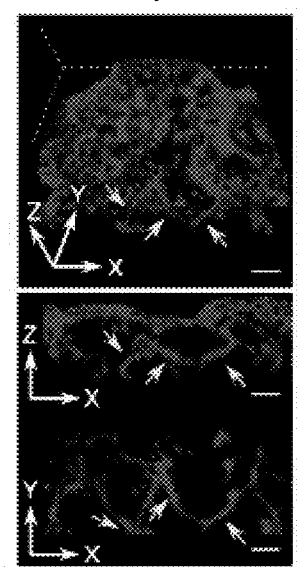
FIG. 6D shows 3D rendering and corresponding maximum-intensity projected images of HUVEC-laden constructs incubated for 7 days. Yellow arrows indicate the capillary-like prevascular structures formed by HUVECs within the constructs. Scale bars, 50 μm.

To evaluate their potential to serve as a biological scaffold and induce vascularization, the 3D MSC spheroid-derived dECM was repopulated with HUVECs. For cell seeding, 3D dECM scaffolds were added to a tube that contained HUVEC suspensions and incubated at 37° C. for 60 min before being transferred into ultralow-attachment plates. As shown in the confocal images, the HUVECs were able to adhere to the dECM scaffolds after 1 h (see FIG. 6A). As time progressed, the cells proliferated on the dECM scaffolds (see FIG. 6A). Moreover, the migration and ingrowth of HUVECs into the scaffold was verified by observing the widest cross-section (equatorial plane) of the construct (see FIG. 6B), demonstrating the capacity of 3D MSC spheroid-derived dECM to act as a scaffold system and thus become a cell-laden construct. Furthermore, reconstructed 3D confocal images from serial optical sections demonstrated the cell-driven macroassembly of multiple 3D cell-seeded dECM scaffolds (see FIG. 6C), suggesting their potential to serve as building blocks for engineering large constructs. After a 7-day culture, capillary-like prevascular structures formed by HUVECs were observed within the constructs (see FIG. 6D).

Example 6

Evaluation of Angiogenesis In Vivo Induced by 3D MSC Spheroid-Derived dECM

The operation process of in vivo bioactivity evaluation used in this example is as follows. Animal experiments were performed according to the Guidebook for the Care and Use of Laboratory Animals (third edition), published by the Chinese-Taipei Society of Laboratory Animal Sciences in 2000. The experimental protocol was reviewed and approved by the Institutional Animal Care and Utilization Committee, National Tsing Hua University, Hsinchu, Taiwan. Six-week old female nude mice (BALB/cAnN.Cg-Foxn1$^{nu}$/CrlNarl) were purchased from the National Laboratory Animal Center, Nangang, Taiwan. To perform implantation, 400 3D dECM scaffolds were thoroughly mixed with 20 μL of GFR Matrigel and incubated at 37° C. for 30 min before being engrafted subcutaneously into the dorsal flanks of nude mice. After 1 week, the animals were euthanized by $CO_2$ inhalation, and the implants were retrieved, fixed in 10% phosphate-buffered formalin (Sigma-Aldrich), and embedded in paraffin to prepare 7-μm thick sections. Tissue sections were stained with hematoxylin and eosin or immunostained using antibodies against von Willebrand factor (vWF) or α-smooth muscle actin (aSMA; both from Agilent Technologies).

Figure 7A:
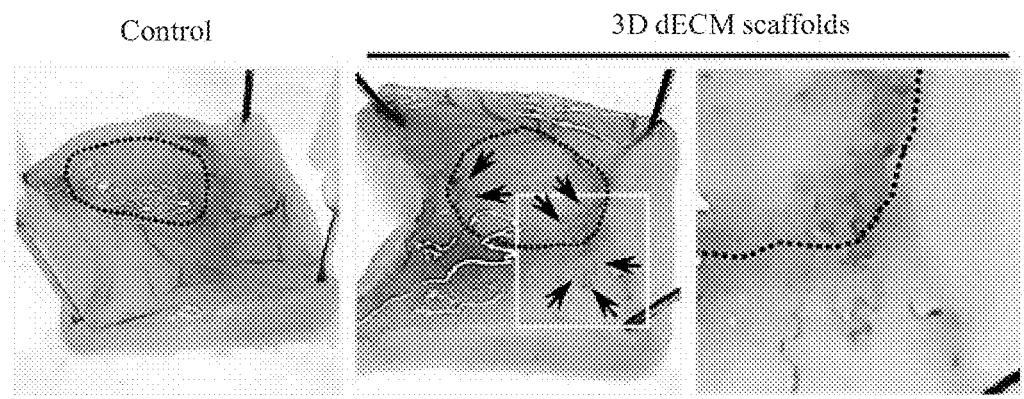
FIG. 7A shows photographs of test samples retrieved at one week after subcutaneous implantation. Dotted area indicates the implanted Matrigel with dECM scaffolds. White box is enlarged in right panel. Arrows indicate nascent blood vessels.
Figure 7B:
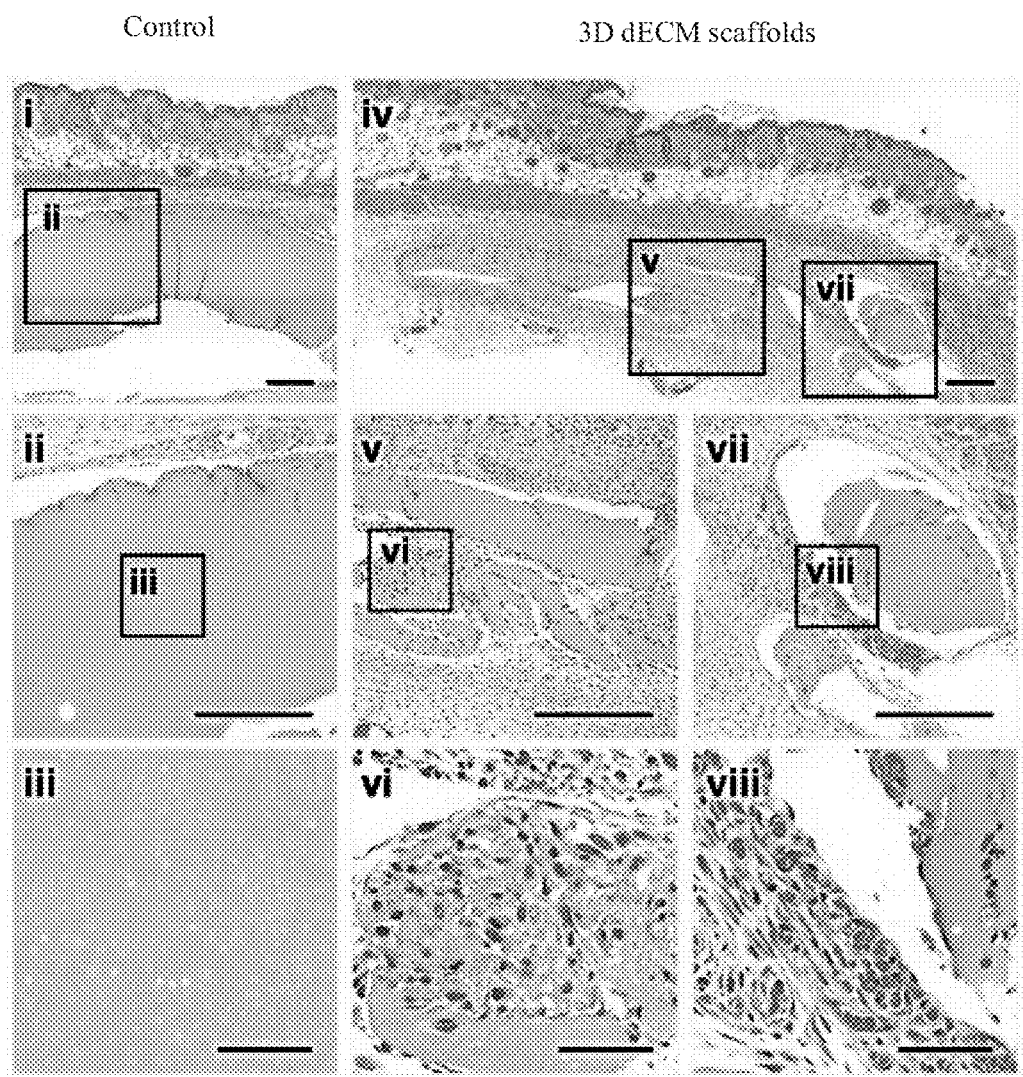
FIG. 7B shows hematoxylin and eosin staining images of test samples retrieved at one week after subcutaneous implantation. Scale bars in (i), (ii), (iv), (v) and (vii): 500 µm. Scale bars in (iii), (vi) and (viii): 100 µm.
Figure 7C:
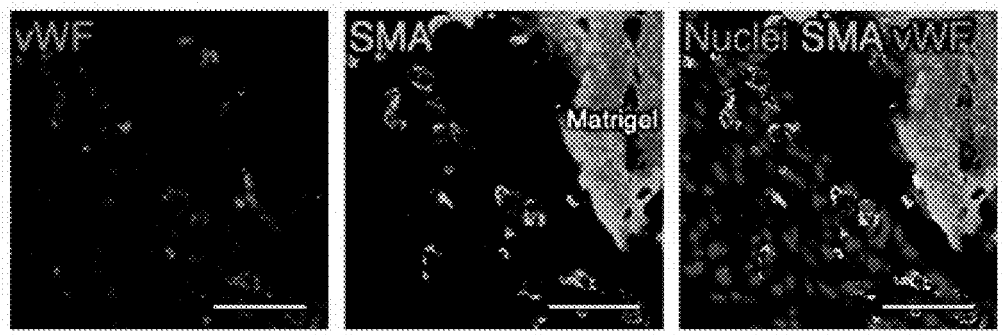
FIG. 7C shows immunofluorescence images of von Willebrand factor (vWF) and smooth muscle actin (SMA) in (FIG. 7B: viii). Scale bars, 50 µm.

The developed 3D dECM scaffolds were mixed with GFR Matrigel and subcutaneously implanted in nude mice via local injection to evaluate their in vivo bioactivity. Animals that received plain GFR Matrigel were used as controls. Both implants adhered to the inside of the skin. At day 7, empty Matrigels exhibited a translucent gross appearance with no obvious vessels growing into the implant (see FIG. 7A). 3D dECM scaffolds carrying Matrigels exhibited an opaquer overall appearance with few superficial vessels growing into the edges of the implants (see FIG. 7A). The harvested Matrigels were processed for histological analysis. The results of H&E staining show that the interior of the engrafted empty Matrigel remained overall free of cells and vasculature (see FIG. 7B), whereas remarkable cell infiltration and vessel formation could be found in the gel containing the 3D dECM scaffolds (see FIG. 7B). This was further confirmed by vWF (endothelial cells) and aSMA (perivascular cells) staining of infiltrated cells (see FIG. 7C), demonstrating the bioactive potential of the scaffolds to attract cells and induce vascularization in vivo.

Figure 8:
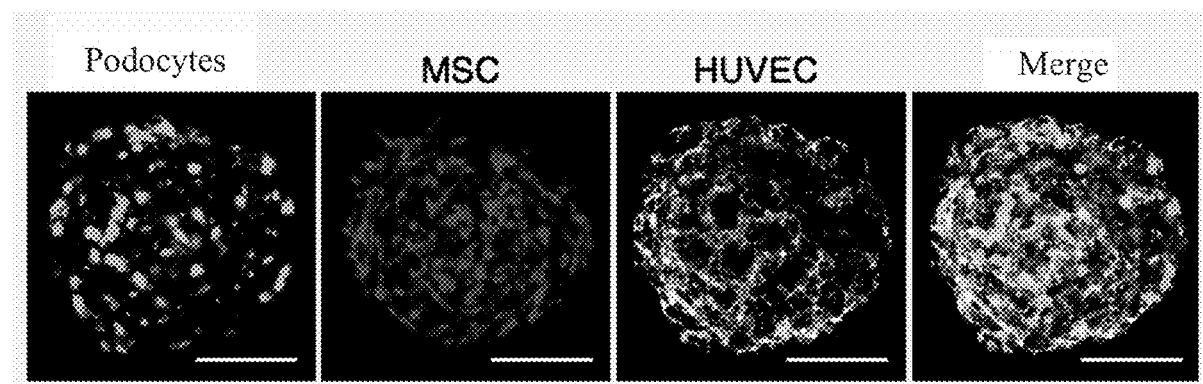
FIG. 8 shows that different types of cells (including podocytes, mesenchymal stem cells (MSC) and human umbilical cord vein endothelial cells (HUVEC)) can all construct three-dimensional cell spheroids.

In another embodiment, two or more cell types can be combined to construct a three-dimensional cell spheroid. FIG. 8 shows that different types of cells (including podocytes, mesenchymal stem cells (MSC) and human umbilical cord vein endothelial cells (HUVEC)) can all construct three-dimensional cell spheroids.

In summary, the effect of the decellularized extracellular matrix (dECM) of the present invention is that since the matrix is made of three-dimensionally cultured cells, its components and microstructure are quite similar to those in biological tissues. The experimental results show that cells can be effectively attached to the surface of the three-dimensional decellularized extracellular matrix and perform proliferation. Since the three-dimensional decellularized extracellular matrix contains bioactive components secreted by many cells, such as growth factors, cytokines, and exosomes, it has the function of regulating the behavior of subsequent attached cells. By changing the types of cells that construct three-dimensional cell spheroids or controlling cell behavior, the composition of the bioactive molecules remaining in the three-dimensional decellularized extracellular matrix is not the same, so it has a wide range of applications, such as the use of stem cells. When a three-dimensional spheroid is established, the remaining bioactive molecules can contribute to the occurrence of angiogenesis and tissue regeneration. With the macromolecular crowding (MMC) induced by carbohydrate-based macromolecules, the total amount of extracellular matrix (ECM) and growth factor secretion in the three-dimensional cell spheroids can be significantly increased, which in turn makes the content of ECM molecules and growth factors in the subsequent derived decellularized extracellular matrix increased, further enhancing the biological activity of the decellularized extracellular matrix. In addition, each three-dimensional decellularized extracellular matrix can be regarded as a small scaffold with the same size as the three-dimensional cell spheroid before decellularization, so three-dimensional decellularized extracellular matrix with different diameters can be prepared according to requirements. After the cells are cultured in a three-dimensional decellularized extracellular matrix, they can be used as a carrier for cell transmission (for example, transplanting a three-dimensional decellularized extracellular matrix containing cells to the site to be treated by injection), a plurality of three-dimensional decellularized extracellular matrices can be assembled into a large structure in a variety of ways. Since the three-dimensional decellularized extracellular matrix is relatively easy to manufacture in large quantities, the large-scale stents formed by polymerization are not limited in shape and size, and can be highly customized. Furthermore, because the cells are first cultured on individual three-dimensional decellularized extracellular matrix, the aggregated cells can be evenly distributed in the entire large scaffold structure, solving the uneven distribution of cells encountered in traditional tissue engineering.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for preparing a decellularized extracellular matrix, comprising:
   (a) co-culturing a plurality of human umbilical cord blood mesenchymal stem cells (MSCs) and human umbilical cord vein endothelial cells (HUVECs) in vitro for 2-3 days to construct a three-dimensional cell spheroid, wherein the three-dimensional cell spheroid secrets an extracellular matrix, wherein the three-dimensional cell spheroid is fabricated with a total of 7,000 cells including a combination of MSCs and HUVECs per spheroid;
   (b) using at least one carbohydrate-based macromolecule to induce macromolecular crowding (MMC) for increasing deposition of the extracellular matrix and amount of the at least one bioactive component by the plurality of MSCs and HUVECs during constructing the three-dimensional cell spheroid, wherein the at least one carbohydrate-based macromolecule is 2-(chloromethyl)oxirane;(2R,3R,4S,5S,6R)-2-[(2S,3S,4S,5R)-3,4-dihydroxy-2,5-bis(hydroxymethyl)oxolan-2-yl]oxy-6-(hydroxymethyl)oxane-3,4,5-triol, and the 2-(chloromethyl)oxirane;(2R,3R,4S,5S,6R)-2-[(2S,3S,4S,5R)-3,4-dihydroxy-2,5-bis(hydroxymethyl)oxolan-2-yl]oxy-6-(hydroxymethyl)oxane-3,4,5-triol has an average molecular weight of 400 kDa; and
   (c) removing cellular and nuclear contents from the three-dimensional cell spheroid to obtain the decellularized extracellular matrix, wherein the decellularized extracellular matrix comprises at least one bioactive component, a collagen I, a fibronectin, and a laminin, wherein the three-dimensional cell spheroid is subjected to a decellularization treatment by using an alkaline non-ionic surfactant and a deoxyribonuclease;
   wherein the decellularized extracellular matrix has a three-dimensional spherical structure;
   wherein the alkaline non-ionic surfactant is 2-[4-(2,4,4-trimethylpentan-2-yl)phenoxy]ethanol, and the deoxyribonuclease is DNase I; and
   wherein the at least one bioactive component is vascular endothelial growth factor (VEGF) or an exosome.

* * * * *